(12) United States Patent
Siewert

(10) Patent No.: US 6,382,830 B1
(45) Date of Patent: May 7, 2002

(54) METHOD FOR DETERMINING THE QUALITATIVE COMPOSITION OF THE ORGANIC SOIL SUBSTANCE OF MINERAL SOILS

(76) Inventor: Christian Siewert, Drosselstieg 4, D-10318 Berlin (DE)

( * ) Notice: Subject to any disclaimer, the term of this patent is extended or adjusted under 35 U.S.C. 154(b) by 0 days.

(21) Appl. No.: 09/601,256

(22) PCT Filed: Jan. 30, 1998

(86) PCT No.: PCT/EP98/00509

§ 371 Date: Aug. 22, 2000

§ 102(e) Date: Aug. 22, 2000

(87) PCT Pub. No.: WO99/39180

PCT Pub. Date: Aug. 5, 1999

(51) Int. Cl.⁷ .......................... G01N 25/00; G01N 5/04; G01N 33/24
(52) U.S. Cl. ............................ 374/45; 374/14
(58) Field of Search ............... 374/45, 14, 10

(56) References Cited

U.S. PATENT DOCUMENTS 5,085,527 A * 2/1992 Gilbert .................. 374/14

FOREIGN PATENT DOCUMENTS

| DE | 249972 A1 | 9/1987 | | |
|----|-----------|--------|---|---|
| DE | 252890 A1 | 12/1987 | | |
| DE | 259460 A1 | 8/1988 | | |
| DE | 196 38 731 C1 | * 4/1998 | .................. | 374/45 |
| SU | 1 386 899 A | * 4/1988 | .................. | 374/45 |

OTHER PUBLICATIONS

Gall, F Et Al: "Determination of the organic matter, metal carbonate and mobile water in soils . . . ",J Therm Anal, vol. 42, No. 5, Nov. 1994, pp. 1007–1016.*

Leinweber Peter Et Al: "Organo–mineral soil clay fractions in fertilization experiments . . . ", Appl Clay Sci, vol. 8, No. 4, Sep. 1993, pp. 295–311.*

Golebiowska D Et Al: Proc 5th Nordic Symp Humic Substances . . . Humor/Humex Project, Lund, Sweden, vol. 22, No. 5, Jun. 1995, pp. 495–500.*

Friedrich Et Al, J Therm Anal, vol. 46, No. 6, John Wiley & Sons Ltd, Chichester, England, Jun. 1996, pp. 1589–1597.*

Database WPI Section Ch, Week 8843, Derwent Publications Ltd., London, GB; Class J04, AN 88–305584, XP002077979, Abstract of SU 1 386 899 A, Apr. 1988.*

C.Siewert; Okosystemorientierte Grundlagen der Humusqualitätsbestimmung; Arch. Acker Pfl.Boden, 1994; vol. 38, pp. 179–193.

C.Angehrn–Bettinazzi et al; Thermogravimetry as a Method for Distinguishing Various Degrees of Mineralisation in Macromorphologically–defined Humus Horizons; Pfanzenernähr Bodenk. vol. 151 1988; pp. 177–183.

* cited by examiner

Primary Examiner—Diego Gutierrez
Assistant Examiner—Stanley J. Pruchnic
(74) Attorney, Agent, or Firm—Norris, McLaughlin & Marcus

(57) ABSTRACT

The invention relates to a method of determining the qualitative composition of soil organic matter (SOM) of mineral soils using thermogravimetry, i.e., by subjecting a soil sample of constant weight to thermogravimetric analysis in the usual way and forming the quotient of the overall weight loss of the sample during heating from 200° C. to 450° C. and the overall weight loss of the sample during heating from 95° C. to 190° C. The method is straightforward and cost-effective, providing reliable figures for all mineral soils, regardless of region, climatic zone, or type of utilization.

2 Claims, 2 Drawing Sheets

METHOD FOR DETERMINING THE QUALITATIVE COMPOSITION OF THE ORGANIC SOIL SUBSTANCE OF MINERAL SOILS

BACKGROUND OF THE INVENTION

The invention relates to a method of determining the qualitative composition of soil organic matter (SOM) of mineral soils using thermogravimetry. The method is straightforward and cost-effective, providing reliable figures for all mineral soils, regardless of climatic zones, geological base substrates, soil genesis, type of utilization, and other effects.

One of the most important features of mineral soils is the soil organic matter. The term "soil organic matter" encompasses any organic compound contained in soil, with the exception of living biomass. The SOM is composed of humus, dead vegetable and animal biomass, water-soluble organic compounds (e.g. carbohydrates, amino acids, microbial exoenzymes, lipides, vegetable and animal hormones, etc.), as well as other nonliving organic substances or organomineral components.

The term "humus" characteristics all those organic components of mineral soils, which accumulate during soil formation of soil genesis. They differ from all the other organic substances by their soil-specific character.

A wide variety of traditional methods, particularly of analyzed humidified SOM components, are known. They are intended to identify single components, using physical, chemical or biological procedures, so as to elucidate the relations between SOM and individual soil properties and, in particular, soil fertility.

In view of the ecological aspects in soil scientific research, there was an increasing orientation towards SOM components, easily degradable by microbes, with the aims of reducing ecological problems of industrial utilization of soil (e.g. pollution of water with plant nutrients), e.g. by reduced use of mineral fertilizers and optimized technological efforts (e.g. soil treatment), describing the behavior of soil pollutants, and analyzing other effects (e.g. acidification of forest soils). The humidified components of the SOM being relatively stable were deemed to be of minor importance in this context.

Similarly, the related development of methods for rating the quality of SOM components was directed to the identification of individual groups of substances or compounds having a direct relation to current local problems.

No information as to the general properties, function or behavior or SOM could be derived from these methods. For this reason, no methods are known to date which enable a generally applicable determination of the qualitative composition of SOM.

For example, DD 249 972 A1 and DD 252 890 A1 describe methods of determining the convertibility of the soil organic matter, wherein the sparingly mineralizable humic acids are removed, thus enabling the determination of readily mineralizable components of the SOM with high accuracy. In this way, an improved calculation of the annual nutrient liberation from the soil is possible. Relations to classification features of soils, to individual soil formation processes or properties of soils in separate climatic zones, to the functions of the soils within the biosphere, or to principles in the succession of ecological systems cannot be derived from the results of these methods.

DD 259 460 A1 includes a process which uses the varying significance of the thermal stability of humidified and non-humidified components to assess the biological availability and thus, the biological utilizability of convertible components. This process supplements methods for the quantitative determination of convertible components by a qualitative parameter, but is still limited to individual components of SOM and dependent processes of plant nutrient liberation.

Similar conclusions result from investigations on the thermal stability and biological degradability of plant substances (Siewert, C., Archiv Für Acker—and Pflanzenbau und Bodenkunde, 1994, Vol. 38, pp. 179–193). The results suggest the suitability of thermogravimetry in the semi-quantitative detection of biologically convertible components and other features (e.g. hygroscopicity) in base materials of the soil organic matter. However, a transfer of these conclusions to the soil organic matter or to characterize the qualitative composition of the soil organic matter is not possible by means of the above-described procedure.

Numerous problems in current soil research arise from the absence of a generally applicable SOM quality assessment. To date, the presence of diverse classification systems with limited mutual compatibility impedes a worldwide comparison and an integrated interpretation of soil-related results, as well as description of the general functions of soils and, in particular, of the SOM in ecological systems.

SUMMARY OF THE INVENTION

It was therefore the object of the invention to provide a straightforward, cost-effective method of determining the quality of soil organic matter, which method could be used for mineral soils of all regions, climatic zones and types of utilization and would not require an expensive material identification of individual components of the SOM but rather, would be oriented on generally applicable, evolutionary principles of current soil formation.

It has been found that the object of the invention can be accomplished by means of a straightforward and cost-effective thermogravimetric method in accordance with claim 1.

DESCRIPTION OF THE PREFERRED EMBODIMENT

According to the invention, the air-dried soil sample to be examined is subjected to thermogravimetric analysis after storage to constant weight as a thin layer at a constant and relatively high humidity of more than 50%. Storage at 60–95% relative humidity is particularly preferred. Air drying of the sample preferably is performed below 30° C. and more than 50% relative humidity. In thermogravimetric analysis, the sample is heated from 20° C. to more than 960° C. under aerobic conditions, and the weight loss is recorded. The heating rate is selected between 1° C. and 50° C. per minute so as to effect heating of the entire sample volume rapidly, but as simultaneously as possible.

Based on the new finding that humic substances determine the composition of the SOM via buffering the biological activity of microbial exoenzymes and that this effect depends on climatic factors and the clay content, the SOM quality can be determined using the quotient of the overall thermogravimetric weight loss between 200° C. and 450° C. (predominant decomposition range of non-humidified, microbially convertible components of SOM) and the overall thermogravimetric weight loss between 95° C. and 190° C. (weight loss by liberation of water). Preferably, the weight loss quotient according to the invention is determined by dividing the weight loss between 295° C. and 305° C. by the weight loss between 135° C. and 145° C. (predominant decomposition range of buffered exoenzymes). The weight loss quotient describes the amount of non-humic substances in SOM, relative to the amount of water bound in the humic substances, and is independent of the clay content, being valid for all mineral soils, regardless of region, climatic zone or type of soil utilization.

Where weight losses of >1 are found according to the invention, soils are concerned wherein the microbially convertible components of the SOM (non-humic substances) have been accumulated by the buffering effect of humic substances at constant soil moisture, and wherein only small amounts of buffered exoenzymes or none are present (e.g. brown soils under natural forest vegetation).

Where weight losses of <1 are found according to the invention, soils are concerned wherein the amount of exoenzymes is higher than the amount of non-humic substances. These features are characteristics for soils with highly varying soil moisture (e.g. black soils under natural prairie vegetation). They are also found in all those soil horizons poorly supplied with convertible organic residues as a result of soil genesis, with otherwise favorable living conditions for soil microorganisms (horizons below A horizon), i.e., in layers including low amounts of convertible components as a result of soil genesis.

Figure 1:
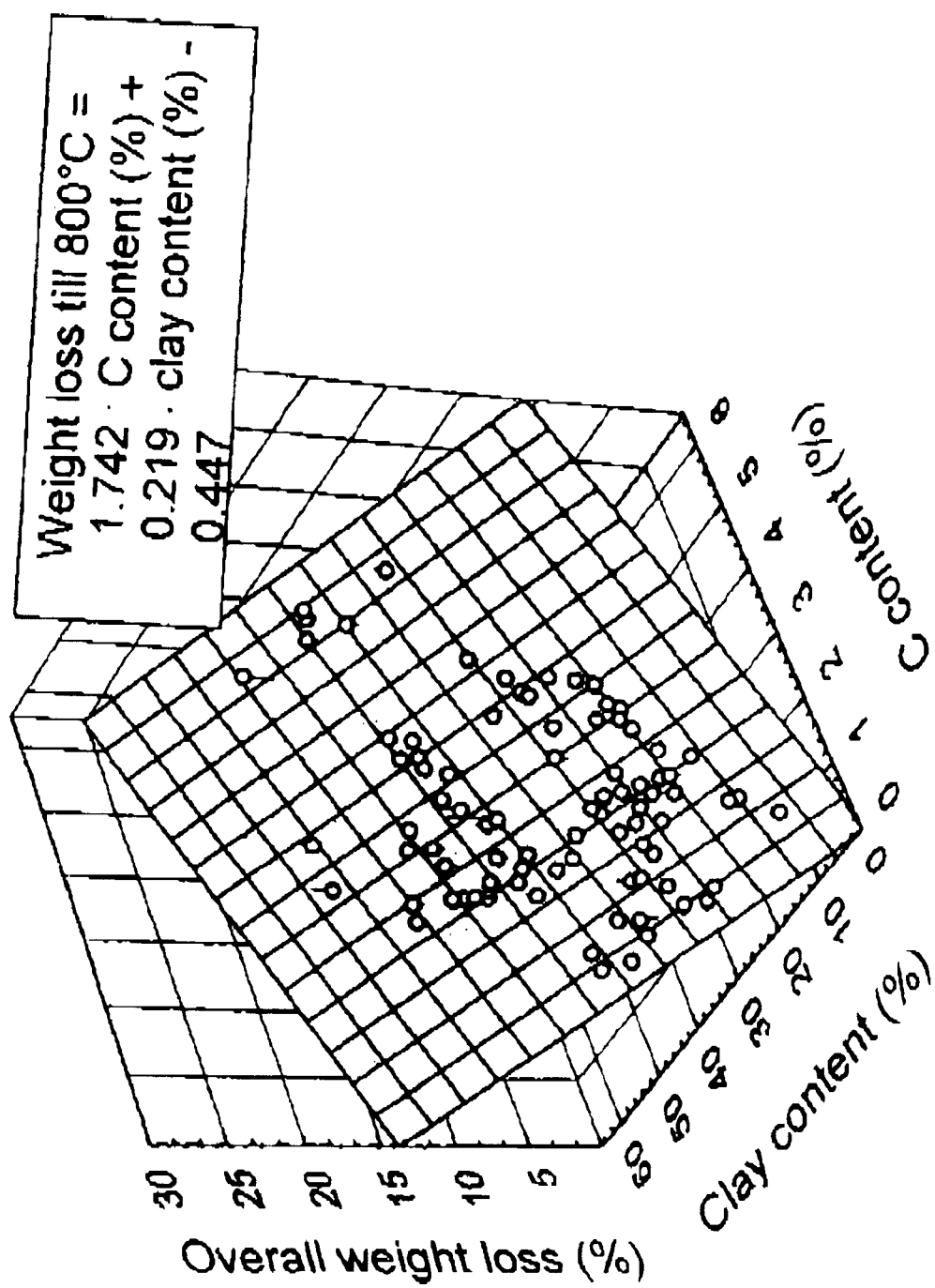
FIG. 1—a graph showing determination of the weight ratio of humidified organic components of the SOM by means of the clay-dependent weight losses.
Figure 2:
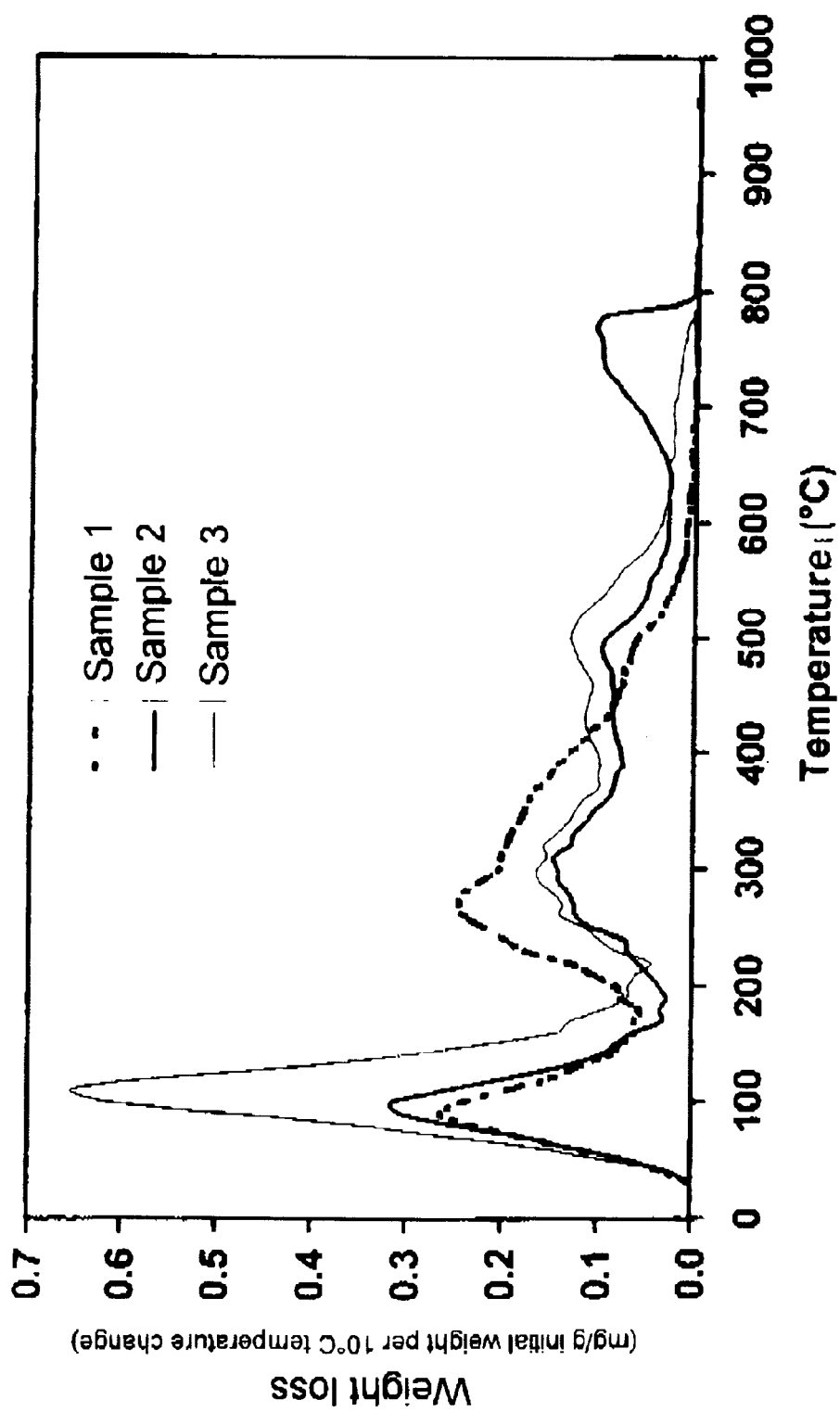
FIG. 2—a chart for selected measured values of thermogravimetric analysis.

The weight ratio of convertible components of the SOM can be quantified as well using the close relationship between the thermogravimetric weight losses during heating from 20° C. to more than 960° C. (preferably from 20° C. to 800° C.) and the clay content and the content of organic carbon (see FIG. 1), and the determination of the weight ratio of humidified organic components of the SOM by means of the clay-dependent weight losses. It is calculated from the overall weight loss minus the weight losses of clay-dependent components of the SOM, using the coefficient for the effect of the clay content on the overall weight loss as illustrated in FIG. 1, and minus the weight loss due to carbonates.

To convert the weight losses of convertible organic substance into the amount of convertible carbon, a factor expressing the mean weight loss of SOM per %C in the soil can be determined. It is calculated by dividing the overall weight loss till 800° C. minus the weight losses due to hygroscopicity for water by the C content of the soil in percent. Division of the weight losses of convertible substance by said factor provides information on the content of convertible carbon in percent in the soil.

The determination of the weight loss quotient according to the invention, in combination with the determination of convertible amounts of SOM enables a well-aimed utilization of the specifics of nutrient liberation for productive soil utilization (forestry and agriculture) and objects of soil protection. These options will be illustrated hereinafter with reference to specific examples.

For example, when detecting equal weight loss quotients in two adjacent soils under the same soil climatic conditions, the amount of convertible substances is proportional to the amount of plant nutrients that can be liberated by biological conversion processes. If, in contrast, the determination of the amount of convertible substances furnishes equal values and the weight loss quotient is different, a slower liberation of nutrients in the soil having higher weight loss quotient is to be expected as a result of a more uniform soil moisture on an average.

Changes in the weight loss quotient in the course of a year are indicative of changes in the SOM quality due to the weather. For example, a drop in the weight loss quotient during the summer months as a result of varying soil moisture at a constant level of convertible substance is indicative of an increase of the amount of buffered exoenzymes in the SOM. With increasing soil moisture in autumn or during the winter months, the latter give rise to a massive liberation of nutrients which either may be utilized by overwintering cultures or may pollute the groundwater as a result of leaching. Following a uniformly moist summer or in case of a minor decrease of the weight loss quotient, however, no liberation of nutrients has to be expected during the cold season or in case of increasing soil moisture, so that—for the purpose of crop management—overwintering cultures can be fertilized at a lower risk of nutrient displacement.

The variation of the weight loss quotient is highest when depending on the climate and the effect of groundwater on the soil moisture, it is less when depending on the vegetation, the clay content and other factors, and it is least in the course of a year. Thus, if the soil climatic conditions (climate, effect of groundwater, vegetation) are known, diagnosing the soil types is possible, using the weight loss quotient or the SOM quality expressed therein. In agricultural soils, an assessment of the condition of supply with organic substance is possible. On the other hand, if the type of soil, the soil utilization and supply of convertible organic residues are known, the weight loss quotient permits conclusions as to the specifics of soil formation, particularly those relating to the mean variability of moisture conditions.

Furthermore, conclusions as to the ecological suitability of a particular soil for various types of utilization are possible. Thus, for example, high weight loss quotients are indicative of constant moisture conditions and slow liberation of nutrients, which in most cases is more similar to the withdrawal dynamics of a forest vegetation. In contrast, exceedingly small weight loss quotients, particularly in combination with high absolute values for the content of convertible substance, are an indication that the soil is suitable for agricultural cultivation with a short, prairie-like vegetation period (e.g. most types of grain).

As to the classification of soils, small weight loss quotients are indicative of varying moisture conditions as are characteristic e.g. for $A_h$ horizons (humus accumulation horizons) of podzolic and black soils. On the other hand, large weight loss quotients are typical of, inter alia, brown soils and soils of the evenly moist tropics (under natural forest vegetation). Variations in the weight loss quotient are also accompanied by variations in the coloration intensity (color intensity of the SOM per C content), which can be used for comparative diagnostics of the SOM quality if equal levels of coloring cations (e.g. Fe, Mn) are present. This allows for options of developing field methods which can be subjected to local calibration and adaptation by means of the thermogravimetric method.

Without intending to be limiting, the invention will be described with reference to the embodiments hereinbelow.

Embodiments

The following samples were analyzed:

1. A parabrown soil from the Hildesheim Plain (Germany) on loess under old beech mixed forest
2. A parabrown soil from the Hildesheim Plain on loess under agriculture utilization, situated immediately adjacent to sample 1 (same geographical and climatic base conditions)
3. A brown black soil of keuper material under agricultural utilization from the Weimer region (Germany)

The thermogravimetric analyses of these samples were carried out on a rebuilt "derivatograph" by the Hungarian "MOM" company, and the results were verified by the same analyses using a thermobalance supplied by Mettler-Toledo GmbH (TGA/SDTA 851$^e$). Heating was effected from room temperature (20–25° C. to more than 960° C. at a heating rate of 5° C. per minute under aerobic conditions. Temperature and weight loss were recorded continuously during the thermogravimetric analysis. The initial weight of the soil samples was 1700 mg (with TGA/SDTA 851$^e$: 900 mg). To prepare the analyses, the air-dried soil samples were stored in a layer 3 mm in thickness at maximum and at 76% relative humidity for 10 days to ensure adjustment of equal moisture conditions in all of the samples.

TABLE 1

Selected measured values of thermogravimetric analysis

Overall weight loss in mg/g initial weight for the temperature ranges

| from (° C.) | 295 | 135 | 30 | 105 | 355 | 415 | 660 | 30 |
|---|---|---|---|---|---|---|---|---|
| to (° C.) | 305 | 145 | 800 | 115 | 365 | 425 | 970 | 190 |
| Column | 1 | 2 | 3 | 4 | 5 | 6 | 7 | 8 |
| Sample 1 | 0.205 | 0.088 | 6.90 | 0.195 | 0.175 | 0.107 | 0.16 | 2.05 |
| Sample 2 | 0.143 | 0.098 | 6.77 | 0.256 | 0.092 | 0.085 | 0.97 | 2.27 |
| Sample 3 | 0.165 | 0.307 | 9.38 | 0.653 | 0.116 | 0.113 | 0.40 | 4.54 |

Based on Table 1, the SOM quality was determined by forming the quotient of the weight losses between 295° C. and 305° C. (column 2) and the weight losses between 135° C. and 145° C. (column 3) for each sample. The following calculation was obtained for sample 1: 0.205/0.088=2.33. An analogous procedure was carried out for samples 2 and 3, thereby obtaining an SOM quality of index of 1.46 for sample 2, and of 0.54 for sample 3.

The SOM quality values of sample 1 serve as a basis for comparison. They are typical of $A_h$ of horizons (humus accumulation horizons) of soils in moderate humid climates under forest, or of brown soils under natural vegetation. The agricultural utilization of the same soil (sample 2) results in a significant reduction of convertible carbon, while the content of inert or humidified carbon remains unchanged (difference of C content and C of convertible substance). This explains the significantly lower weight loss quotient for the SOM quality. In sample 3, the latter again is significantly lower, reaching magnitudes of black soils, i.e., soils with markedly varying moisture and prairie vegetation. In addition to agricultural utilization, the cause for this weight loss quotient in sample 3, which is small for a humid climatic region, is a significantly increased variability of soil moisture, resulting from lesser precipitation in the respective region and from a lower water-holding capacity of the soil rich in clay, compared to samples 1 and 2 on loess.

For soil utilization, these results allows the conclusion that brown-black soils are better suited for agricultural production, or, in particular, for cultures having a short vegetation period (original prairie plants) because—in contrast to sample 2—more rapid liberation of nutrients is to be expected when supplying organic substance. However, the amount of convertible substance is clearly below the normal level of black soils (not depicted). Accordingly, the utilization of the crop potential of sample 3 requires a significant higher supply of organic substance than practiced so far, i.e., compared to sample 2, the deficiency in organic fertilizing materials is considerably higher as a result of utilization (in this case a consequence of more intense filed utilization over decades).

In contrast, owing to the remarkable buffering of nutrient resources, sample 1 presents the best preconditions for slow and sustained supply of nutrients as is favorable in forestry concerns and to prevent pollution of the groundwater (decrease of nutrient displacement).

In addition, the weight loss quotient can be utilized as a classification feature, because values above 1 in the $A_p$ horizon (plow horizon, samples 1 and 2) only occur in brown soils and only in rare cases in lessivated (clay-soaked) and podsolized soils (soils with clay destruction). In this respect, the results of quality assessment confirm the correctness of sample classification according to individual types of soil and climatic zones (the latter only where the vegetation is known), even without knowledge about the profile structure. In contrast, the low weight quotient in sample 3 is indicative of a classification as black soil. As long as additional samples are not included, however, statements as to which quality quotient is characteristic for such a soil under natural vegetation are not possible. As a result of the detected insufficient supply with organic substance, however, values significantly closer to 1 can be expected, so that this can only be a transition soil from a black to a brown soil. This conclusion is in conformity with the classification of this soil as a brown-black soil, which has been made with reference to the profile structure. Thus, a judgement as to the type of soil is possible in sample 3 as well using such quality assessment, together with information on agricultural utilization and the most significant climatic conditions of soil formation.

What is claimed is:

1. A method of determining the qualitative composition of soil organic matter (SOM) of mineral soils, comprising:

subjecting a soil sample of constant initial weight to thermogravimetric analysis wherein the sample is heated through a first temperature range between 95° C. to 190° C., resulting in a first overall weight loss of the sample, and through a second temperature range between 200° C. to 450° C., resulting in a second overall weight loss of the sample; and forming the quotient of the second overall weight loss and the first overall weight loss, said quotient corresponding to the qualitative composition of soil organic matter (SOM) of mineral soils.

2. The method according to claim 1, wherein said second overall weight loss of the sample is determined from the overall weight loss measured during heating from 295° C. to 305° C. and said first overall weight loss of the sample is determined from the overall weight loss measured during heating from 135° C. to 145° C.

* * * * *